United States Patent
Chang et al.

(10) Patent No.: US 6,541,408 B2
(45) Date of Patent: Apr. 1, 2003

(54) ZEOLITE CATALYSTS HAVING STABILIZED HYDROGENATION-DEHYDROGENATION FUNCTION

(75) Inventors: Clarence D. Chang, Princeton, NJ (US); Paul G. Rodewald, Jr., Rocky Hill, NJ (US)

(73) Assignee: ExxonMobil Oil Corp., Fairfax, VA (US)

( * ) Notice: Subject to any disclaimer, the term of this patent is extended or adjusted under 35 U.S.C. 154(b) by 0 days.

(21) Appl. No.: 10/041,215

(22) Filed: Oct. 29, 2001

(65) Prior Publication Data

US 2002/0091293 A1 Jul. 11, 2002

Related U.S. Application Data

(62) Division of application No. 08/995,271, filed on Dec. 19, 1997, now Pat. No. 6,346,498.

(51) Int. Cl.$^7$ .......................... B01J 29/06; B01J 21/00; B01J 29/00; C07C 5/22
(52) U.S. Cl. .......................... 502/64; 502/71; 502/74; 502/77; 585/480; 585/481; 585/482
(58) Field of Search .......................... 502/66, 71, 74, 502/77, 325, 326, 328, 329, 330, 331, 337, 338, 339, 340, 343, 344, 345, 347, 241, 243, 244, 245, 250, 255, 258, 259, 260, 261, 262; 585/480, 481, 482

(56) References Cited

U.S. PATENT DOCUMENTS

| | | | |
|---|---|---|---|
| 3,471,582 A | 10/1969 | Lupfer .................. 260/677 |
| 3,698,157 A * | 10/1972 | Allen et al. ................ 55/67 |
| 3,907,921 A | 9/1975 | Winter, III .............. 260/683.3 |
| 4,039,604 A | 8/1977 | Myers et al. .......... 260/683.68 |
| 4,079,092 A | 3/1978 | Hayes et al. ............. 260/667 |
| 4,100,215 A * | 7/1978 | Chen .................... 260/671 M |
| RE29,948 E | 3/1979 | Dwyer et al. ............. 208/110 |
| 4,145,315 A * | 3/1979 | Rodewald ............... 252/455 Z |
| 4,224,141 A | 9/1980 | Morrison et al. ........... 208/134 |
| 4,229,424 A | 10/1980 | Kokotailo ................ 423/328 |
| 4,312,790 A | 1/1982 | Butter et al. ............. 252/455 |
| 4,465,886 A | 8/1984 | Rodewald ................ 585/467 |
| RE31,919 E | 6/1985 | Butter et al. ............... 502/66 |
| 4,548,914 A | 10/1985 | Chu ....................... 502/85 |
| 4,562,169 A | 12/1985 | Hagerty et al. ............ 502/107 |
| 4,812,222 A * | 3/1989 | Kirker et al. .............. 208/89 |
| 4,851,604 A * | 7/1989 | Absil et al. .............. 585/475 |
| 4,950,835 A * | 8/1990 | Wang et al. ............. 585/467 |
| 5,314,854 A | 5/1994 | Galperin ................. 502/66 |
| 5,321,183 A | 6/1994 | Chang et al. ............ 585/475 |
| 5,349,113 A | 9/1994 | Chang et al. ............ 585/475 |
| 5,349,114 A | 9/1994 | Lago et al. .............. 585/475 |
| 5,365,003 A | 11/1994 | Chang et al. ............ 585/470 |
| 5,365,004 A | 11/1994 | Beck et al. ............. 585/475 |
| 5,367,099 A | 11/1994 | Beck et al. ............. 585/475 |
| 5,382,737 A | 1/1995 | Beck et al. ............. 585/475 |
| 5,403,800 A | 4/1995 | Beck et al. .............. 502/64 |
| 5,406,015 A | 4/1995 | Beck et al. ............. 585/475 |
| 5,464,800 A | 11/1995 | Galperin et al. ........... 502/66 |
| 5,498,814 A | 3/1996 | Chang et al. ............ 585/475 |
| 5,516,736 A | 5/1996 | Chang et al. ............. 502/64 |
| 5,625,103 A | 4/1997 | Abichandani et al. ...... 585/475 |
| 5,665,223 A | 9/1997 | Bogdan .................. 208/138 |
| 5,858,908 A | 1/1999 | Bogdan et al. ............ 502/227 |
| 6,207,871 B1 * | 3/2001 | Hellring et al. ........... 585/475 |

\* cited by examiner

Primary Examiner—Stanley S. Silverman
Assistant Examiner—Cam N. Nguyen

(57) ABSTRACT

A zeolite catalyst suitable for use in shape-selective hydrocarbon conversion processes. The catalyst is modified by incorporation therein of a hydrogenation-dehydrogenation functional metal, followed by gradient selectivation with an organosilicon compound under conversion conditions, wherein the gradient selectivation conditions are characterized by a progressive temperature gradient. The use of a progressive temperature gradient during the in situ selectivation procedure unexpectedly yields a catalyst in which the hydrogenation-dehydrogenation function is stabilized, thereby enabling long duration hydrocarbon conversion processes with low by-product make.

11 Claims, No Drawings

ZEOLITE CATALYSTS HAVING STABILIZED HYDROGENATION-DEHYDROGENATION FUNCTION

This application is a divisional of Ser. No. 08/995,271, filed on Dec. 19, 1997, U.S. Pat. No. 6,346,498, issued Feb. 12, 2002.

BACKGROUND OF THE INVENTION

1. Field of the Invention

The invention relates to improvements in the preparation of catalysts for shape-selective reactive conversions of aromatic hydrocarbon compounds. More specifically, the invention relates to improvements in methods of modifying zeolite catalysts and shape-selective hydrocarbon conversion processes using such catalysts.

2. Description of the Prior Art

The term shape-selective catalysis describes unexpected catalytic selectivities in zeolites. The principles behind shape selective catalysis have been reviewed extensively, e.g., by Chen N Y, Garwood W E, and Dwyer F G, *Shape Selective Catalysis in Industrial Applications*, Marcel Dekker, Inc., New York (1989). Within a zeolite pore, hydrocarbon conversion reactions such as paraffin isomerization, olefin skeletal or double bond isomerization, oligomerization, and aromatic disproportionation, alkylation, or transalkylation reactions are governed by constraints imposed by the channel size. Reactant selectivity occurs when a fraction of the feedstock is too large to enter the zeolite pores to react. Product selectivity occurs when some of the products cannot leave the zeolite channels. Product distributions can also be altered by transition state selectivity in which certain reactions cannot occur because the reaction transition state is too large to form within the zeolite pores or cages. Another type of selectivity results from configurational diffusion where the dimensions of the molecule approach that of the zeolite pore system. A small change in dimensions of the molecule or the zeolite pore can result in large diffusion changes leading to different product distributions. This type of shape selective catalysis is demonstrated, for example, in selective disproportionation of toluene to para-xylene.

Para-xylene is a very valuable commercial product useful in the production of polyester fibers. The catalytic production of p-xylene has received much attention in the scientific community and various methods for increasing catalyst para-selectivity have been described.

The synthesis of p-xylene is typically performed by methylation of toluene over a catalyst under conversion conditions. Examples are the reaction of toluene with methanol as described by Chen et al., *J. Amer. Chem. Soc.* 101:6783 (1979) and toluene disproportionation, as described by Pines in *The Chemistry of Catalytic Hydrocarbon Conversions*, Academic Press, New York, p. 72 (1981). Such methods typically result in the production of a mixture including p-xylene, o-xylene, and m-xylene. Depending upon the para-selectivity of the catalyst and the reaction conditions, different percentages of p-xylene are obtained. The yield, i.e., the amount of feedstock actually converted to xylene, is also affected by the catalyst and the reaction conditions.

The equilibrium reaction for the disproportionation conversion of toluene to xylene and benzene yields about 59% mixed xylenes and benzene, with the balance being toluene. Of the converted product, about 57.6 wt % is mixed xylenes, with the remainder being benzene. The equilibrium distribution of the various xylenes in the mixed xylenes fractions is about 24% para-xylene, about 54% meta-xylene, and about 22% ortho-xylene. Given the limitations in the conversion rate and selectivity of this reaction, the total p-xylene yield (-xylene purity) is only about 8.2%. The unique importance of p-xylene motivates the search for methods of improving conversion and selectivity of this and related reactions.

The para-selectivity of hydrocarbon conversions can be improved by modifying the processing qualities of zeolite catalysts. One method by which the para-selectivity of such catalysts can be improved is by modifying the catalyst through treatment with "selectivating agents." Modification methods have been suggested wherein the catalyst is modified by treatment prior to use to provide a silica coating. For example, U.S. Pat. Nos. 4,477,583 and 4,127,616 disclose methods wherein a catalyst is contacted at ambient conditions with a modifying compound such as phenylmethyl silicone in a hydrocarbon solvent or an aqueous emulsion, followed by calcination. Such modification procedures have been successful in obtaining para-selectivity of greater than about 90%, but with commercially unacceptable toluene conversions of only about 10%, resulting in a yield of not greater than about 9%, i.e., 10%×90%. Such processes also produce significant quantities of o-xylene and m-xylene, thereby necessitating expensive separation processes to separate the p-xylene from the other isomers.

Typical separation procedures include costly fractional crystallization and adsorptive separation of p-xylene from other xylene isomers which are customarily recycled. Xylene isomerization units are then required for additional conversion of the recycled xylene isomers into an equilibrium xylene mixture comprising p-xylene. Those persons who are skilled in the art appreciate that the expense of the separation process is proportional to the degree of separation required. Therefore, significant cost savings are achieved by increasing selectivity to the para-isomer while maintaining commercially acceptable conversion levels.

It is, therefore, highly desirable to provide a regioselective process for the production of p-xylene from toluene while maintaining commercially acceptable toluene conversion levels. But it is also highly desirable to provide processes that are regioselective, or at least highly selective for the production of other types of products whose synthesis can be catalyzed by zeolite-type catalysts. One notable such conversion process is the related ethylbenzene conversion in a feed of ethylbenzene and mixed m- and o-xylenes.

In view of the above considerations, it is clear that existing catalysts and processes for shape selective hydrocarbon conversion are critical to improving the quality and yield of materials suitable for commercial manufacturing. Accordingly, it is one of the purposes of this invention to overcome the above limitations in shape selective hydrocarbon conversion processing, by providing a catalyst for shape selective hydrocarbon conversion processes wherein the catalyst has substantially stabilized hydrogenation-dehydrogenation functionality. The catalyst enables the artisan to perform shape-selective hydrocarbon conversion processes with high product yields and low by-product yields. In particular the catalyst improves the yields and purities of products from aromatics conversion processes such as disproportionations, isomerizations, alkylations, and transalkylations.

SUMMARY OF THE INVENTION

It has now been discovered that these and other objectives can be achieved by the present invention, which provides a catalyst having hydrogenation-dehydrogenation functionality and a method for preparing such a catalyst.

In one embodiment, the invention is a catalyst for use in shape-selective hydrocarbon conversion processes, wherein the catalyst has been modified according to a procedure comprising the steps of:
(a) permeating a hydrogenation-dehydrogenation functional metal into a catalyst to provide a metal-modified catalyst, and
(b) gradient selectivating the metal-modified catalyst under an in situ selectivation protocol that comprises a progressive temperature gradient to provide a functionalized catalyst,
wherein product yield and distribution from a hydrocarbon conversion over the functionalized catalyst is substantially stable with increasing time on stream.

Preferably the catalyst has been modified by permeating into the catalyst a functional metal selected from the group consisting of Groups 3 to 15 of the Periodic Table. More preferably, the functional metal is selected from the group consisting of cadmium, cobalt, copper, gold, iron, mercury, molybdenum, nickel, osmium, palladium, platinum, rhenium, rhodium, ruthenium, silver, zinc, and mixtures thereof.

The catalyst is preferably modified by an in situ selectivation protocol in which the gradient selectivating comprises a stepped or continuous temperature gradient. The progressive temperature gradient can include a lower temperature bound of from about 350° C. to about 460° C., and an upper temperature bound of from about 420° C. to about 550° C. Preferably, the lower temperature bound is from about 380° C. to about 430° C., and the upper temperature bound is from about 450° C. to about 510° C. Moreover, the in situ selectivation protocol preferably further comprises a pressure of from above 0 psig to about 2000 psig, a $H_2/HC$ mole ratio of from 0 to about 20, and a WHSV of from about 0.1 $hr^{-1}$ to about 100 $hr^{-1}$.

The catalyst can also have been further modified by preselectivating the catalyst, i.e., by exposing the catalyst to at least one preselectivation sequence, each preselectivation sequence comprising contacting the catalyst with an organosilicon compound and then calcining the contacted catalyst.

The modified catalyst is preferably a catalyst that comprises a zeolite selected from the group consisting of ZSM-5, ZSM-11, ZSM-12, ZSM-21, ZSM-22, ZSM-23, ZSM-35, ZSM-38, ZSM-48, ZSM-57, and ZSM-58.

In another embodiment, the invention is a method of modifying a catalyst for use in shape-selective hydrocarbon conversion processes, comprising:
(a) permeating a catalytic amount of a hydrogenation-dehydrogenation functional metal into a catalyst to provide a metal-modified catalyst, and
(b) gradient selectivating the metal-modified catalyst under an in situ selectivation protocol that comprises a progressive temperature gradient to provide a functionalized catalyst,
whereby product yield and distribution from a hydrocarbon conversion over the functionalized catalyst is substantially stable with increasing time on stream.

In still a further embodiment, the invention is a process for shape-selective hydrocarbon conversion over a zeolite catalyst, comprising converting a hydrocarbon under conversion conditions over a functionalized catalyst modified according to a method comprising the steps of:
(a) permeating a catalytic amount of a hydrogenation-dehydrogenation functional metal into a catalyst to provide a metal-modified catalyst, and
(b) gradient selectivating the metal-modified catalyst under an in situ selectivation protocol that comprises a progressive temperature gradient to provide a functionalized catalyst,
whereby product yield and distribution from the hydrocarbon conversion over the functionalized catalyst is render substantially stable with increasing time on stream.

The conversion conditions for the hydrocarbon conversion process preferably comprise a temperature of from about 100° C. to about 760° C., a pressure of from above 0 psig to about 3000 psig, a $H_2/HC$ mole ratio of from 0 to about 100, and a WHSV of from about 0.08 $hr^{-1}$ to about 2000 $hr^{-1}$.

These and other advantages of the present invention will be appreciated from the detailed description and examples which are set forth herein. The detailed description and examples enhance the understanding of the invention, but are not intended to limit the scope of the invention.

DETAILED DESCRIPTION OF THE PREFERRED EMBODIMENTS

The present invention is directed to catalysts modified so as to be generally useful in shape-selective hydrocarbon conversion processes including cracking reactions involving dewaxing of hydrocarbon feedstocks; isomerization of alkylaromatics; oligomerization of olefins to form gasoline, distillate, lube oils or chemicals; alkylation of aromatics; conversion of oxygenates to hydrocarbons; rearrangement of oxygenates; and conversion of light paraffins and olefins to aromatics.

The catalyst of the present invention is characterized by having been modified to contain a hydrogenation-dehydrogenation functional metal. Moreover, the hydrogenation-dehydrogenation function of this catalyst is stable under conversion conditions so as to yield consistent levels of product with controlled by-product, e.g., ethylbenzene, make. Specifically, the catalyst has been modified by a procedure that includes introducing platinum or other hydrogenation-dehydrogenation functional metal to the catalyst, such as by ion exchange, and then in situ selectivating the catalyst using a progressive (increasing) temperature gradient. As a result of such modification, the catalyst of the invention has substantially improved shape selectivity and activity in hydrocarbon conversions, which is further characterized by substantially increased stability under hydrocarbon conversion conditions. Details of this invention are provided hereinbelow.

Catalyst System

Catalysts useful in this invention comprise a zeolite, which is also known as a catalytic molecular sieve. The zeolite is preferably an intermediate pore size zeolite. Examples of intermediate pore size zeolites useful in this invention include ZSM-5 (U.S. Pat. No. 3,702,886 and Re. 29,948); ZSM-11 (U.S. Pat. No. 3,709,979); ZSM-12 (U.S. Pat. No. 3,832,449); ZSM-21 (U.S. Pat. No. 4,046,859); ZSM-22 (U.S. Pat. No. 4,556,447); ZSM-23 (U.S. Pat. No. 4,076,842); ZSM-35 (U.S. Pat. No. 4,016,245); ZSM-38 (U.S. Pat. No. 4,406,859); ZSM-48 (U.S. Pat. No. 4,397,827); ZSM-57 (U.S. Pat. No. 4,046,685); and ZSM-58 (U.S. Pat. No. 4,417,780). ZSM-5 zeolites are particularly preferred, and much of the discussion below is directed to these zeolites, but similar consideration apply to other zeolites.

The crystal size of zeolites used herein is preferably greater than 0.1 μm. For the purpose of this invention, ZSM-5 crystals may be divided by crystal size into at least 3 broad groups: small crystal size (e.g., 0.02 μm to 0.2 μm);

medium crystal size (e.g., 0.2 μm to 1 μm); and large crystal size (e.g., greater than 1 μm). Exemplary methods used to prepare controlled crystal size ZSM-5 are given in U.S. Pat. Nos. 4,117,026; 4,526,879; and 4,899,011; 3,702,886; 4,175,114; 4,199,556; 4,341,748; 4,375,458; 5,182,090; 5,243,117; and Great Britain Pat. No. 1,581,513.

The accurate direct measurement of the crystal size of zeolite materials is frequently very difficult. Electron microscopy methods, e.g., SEM and TEM, can be used, but these methods require measurements of a large number of crystals, and, for each crystal measured, values may be evaluated in up to three dimensions. Furthermore, to more completely characterize the crystal size of a batch of crystals, one should calculate the average crystal size as well as the degree of variance from this average in terms of a crystal size distribution. Alternatively, rather than relying upon a complex evaluation of crystal size, crystal size may be expressed in terms of a calculated value of average crystal size obtained by measuring the rate of sorption of 2,2-dimethylbutane at 90° C. and 60 torr (8 kpaa) hydrocarbon pressure. The crystal size is computed by applying the diffusion equation given by J. Crank, *The Mathematics of Diffusion*, Clarendon Press, pp. 52–56 (1957), for the rate of sorbate uptake by a solid whose diffusion properties can be approximated by a plane sheet model.

The zeolite has a Constraint Index within the approximate range of 1 to 12. The method by which Constraint Index is determined is described in U.S. Pat. No. 4,016,218, incorporated herein by reference. Alternatively, the zeolite can be characterized according to pore size. Thus, the zeolite useful according to the invention has a pore size of less than about 7 Å, preferably from about 5 Å to less than about 7 Å.

The zeolite also has a silica to alumina ($SiO_2/Al_2O_3$) molar ratio of at least about 5, preferably from about 12 to about 100, and more preferably from about 20 to about 80. The silica to alumina ratio referred to may be determined by conventional analysis. This ratio is meant to represent, as closely as possible, the molar ratio in the rigid anionic framework of the zeolite crystal and to exclude silicon and aluminum in the binder or in cationic or other form within the channels.

The alpha value of the catalyst should be at least 5. The catalyst of the present invention preferably has an alpha value greater than 100, for example, from about 150 to about 2000. The alpha value is an approximate indication of the catalytic cracking activity of the catalyst compared to a standard catalyst and it gives the relative rate constant (rate of normal hexane conversion per volume of catalyst per unit time.) It is based on the activity of an amorphous silica-alumina cracking catalyst taken as an alpha of 1 (Rate Constant=0.016 sec$^{-1}$). The Alpha Test is described in U.S. Pat. No. 3,354,078 and in *J. Catalysis* 4:522–529 (August 1965): *J. Catalysis* 6:278 (1966); and *J. Catalysis* 61:395 (1980), each incorporated herein by reference as to that description. It is noted that intrinsic rate constants for many acid-catalyzed reactions are proportional to the alpha value for a particular crystalline silicate catalyst (see "The active site of acidic aluminosilicate catalysts," *Nature*, 309(5959) :589–591, (Jun. 14, 1984)). The alpha value of the catalyst may be increased by treating the catalyst with nitric acid or by mild steaming as discussed in U.S. Pat. No. 4,326,994.

The catalyst may be characterized according to its xylene diffusion or xylene sorption properties. In particular, it has been found that the catalyst should possess an equilibrium sorption capacity of xylene, which can be either para-, meta-, ortho-, or a mixture thereof, frequently para-xylene, since this isomer reaches equilibrium within the shortest time, of at least 1 g per 100 g of zeolite measured at 120° C. and a xylene pressure of 4.5±0.88 mm of mercury (493 Paa to 707 Paa) and an ortho-xylene sorption time for 30 percent of the xylene sorption capacity of greater than 1200 minutes (at the same conditions of temperature and pressure) to achieve the desired level of ethylbenzene conversion while maintaining the desired level of xylene loss. The sorption measurements may be carried out gravimetrically in a thermal balance. The sorption test is described in U.S. Pat. Nos. 4,117,026; 4,159,282; 5,173,461; and Re. 31,782, each incorporated herein by reference.

The xylene diffusion properties of the catalyst may be such that, under hydrocarbon conversion conditions, the catalyst is capable of only a limited amount of xylene isomerization. For example, the catalyst may be one that meets the following test: producing less than 12 wt % para-xylene when contacting a feed containing 60 wt % meta-xylene, 20 wt % ortho-xylene, and 20 wt % ethylbenzene at a temperature of 426.7° C., a pressure of 150 psig (1136 kpaa), a weight hourly space velocity (WHSV) of 20 hr$^{-1}$, and a hydrogen to hydrocarbon ($H_2$/HC) molar ratio of 1. In the above test, the catalyst modified according to the invention may even produce smaller amounts of p-xylene, preferably, less than 10 wt % p-xylene, more preferably less than 3 wt %, and still more preferably, less than 1 wt % p-xylene, while converting more than 15 wt %, preferably more than 30 wt %, or more preferably more than 65 wt % of the ethylbenzene, and while producing less than 3 wt % xylene loss, preferably less than 1 wt % xylene loss. Further, the activity of this catalyst may be such that, under the conditions of this test, less than 10 wt % $C_5^-$ material may be produced, preferably less than 7.5 wt %, and more preferably, less than 5 wt % $C_5^-$ material.

The suitable molecular sieve may be employed in combination with a support or binder material such as, for example, a porous inorganic oxide support or a clay binder. For example, it may be desirable to formulate the catalyst of the invention with another material resistant to the temperature and other conditions of the hydrocarbon conversion process. Illustrative examples of binder materials include synthetic or naturally occurring substances as well as inorganic materials such as clay, silica, and/or metal oxides, such as alumina, vanadia, beryllia, thoria, magnesia, titania, zirconia, boria, and combinations thereof. The preferred binder is primarily silica. The metal oxides may be naturally occurring or in the form of gelatinous precipitates or gels including mixtures of silica and metal oxides.

Naturally occurring clays that can be composited with the zeolite include those of the montmorillonite and kaolin families, which families include the subbentonites and the kaolins commonly known as Dixie, McNamee, Georgia, and Florida clays, or others in which the main mineral constituent is halloysite, kaolinite, dickite, nacrite, or anauxite. Suitable clay materials include, by way of example, bentonite and kieselguhr. Such clays can be used in the raw state as originally mined or initially subjected to calcination, acid treatment, or chemical modification.

The relative proportion of suitable crystalline molecular sieve to the total composition of catalyst and binder or support may be from about 1 wt % to about 99 wt %, preferably from about 30 wt % to about 90 wt %, and more preferably from about 50 wt % to about 80 wt %, of the composition.

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, formed using conventional methods, such as extrusion or spray drying.

Procedures for preparing silica bound ZSM-5 are described in U.S. Pat. Nos. 4,582,815; 5,053,374; and 5,182,242. A particular procedure for binding ZSM-5 with a silica binder involves an extrusion process. Another method of silica binding uses a suitable silicone resin, e.g., a high molecular weight, hydroxy functional silicone resin, in a method disclosed in U.S. Pat. Nos. 4,631,267 and 3,090,691. Extrusion aids, such as methyl cellulose materials may also be useful in the preparation of the catalysts of this invention.

The zeolite, either directly or via initial ammonium exchange followed by calcination, may be hydrogen exchanged such that a predominant proportion of its exchangeable cations are hydrogen ions. It is contemplated that more than 50% and preferably more than 75% of the cationic sites of the crystalline aluminosilicate zeolite will be occupied by hydrogen ions. ZSM-5 in the hydrogen exchanged form may be referred to herein as HZSM-5.

Original ions, e.g., alkali or alkaline earth metal, of the as-synthesized zeolite can be replaced in accordance with techniques well known in the art, at least in part, by ion exchange with other ions. Typical ion exchange techniques would be to contact the synthetic zeolite with a solution containing a salt of the desired replacing ion or ions. Examples of such salts include the halides, e.g., chlorides, nitrates, and sulfates. Representative ion exchange techniques are disclosed in a wide variety of patents including U.S. Pat. Nos. 3,140,251 and 3,140,253, each incorporated herein by reference.

Hydrogenation-Dehydrogenation Functional Modification

A hydrogenation-dehydrogenation functional metal is incorporated into the catalyst of the invention. Such metals are known in the art to reduce ethylbenzene by-product in hydrocarbon conversion processes. See U.S. Pat. No. 5,498,814, incorporated herein by reference.

The state of the art is such that the reactor effluent from toluene disproportionation typically contains about 0.5% ethylbenzene by-product. Upon distillation of the reaction products, the level of ethylbenzene in the $C_8$ fraction often increases to about 3–4 percent. This level of ethylbenzene is unacceptable for polymer grade p-xylene since ethylbenzene in the $C_8$ product, if not removed, degrades the quality of fibers ultimately produced from the p-xylene product. Consequently, ethylbenzene content must be kept low. The specification for ethylbenzene in the $C_8$ product has been determined by industry to be about 0.3% or less. The ethylbenzene can be substantially removed by isomerization or by superfractionation processes. Removal of the ethylbenzene by conventional isomerization would be impractical with the present invention since the xylene stream, which advantageously comprises greater than 85% p-xylene, would be concurrently isomerized to equilibrium xylenes reducing the amount of p-xylene in this xylene stream to about 24%. And it is known that the alternative procedure of removing the ethylbenzene by superfractionation is extremely expensive.

Any metal possessing the desired hydrogenation-dehydrogenation function can be used in the modification method of the invention. These are termed "functional metals." Examples of such functional metals include the oxide, hydroxide, sulfide, or free metal (i.e., zero valent) forms of metals in the Groups 3 to 15 of the periodic table. Preferred metals include Group 8, 9, and 10 metals (i.e., Pt, Pd, Ir, Rh, Os, Ru, Ni, Co, and Fe), Group 7 metals (i.e., Mn, Tc, and Re), Group 6 metals (i.e., Cr, Mo, and W), Group 15 metals (i.e., Sb and Bi), Group 14 metals (i.e., Sn and Pb), Group 13 metals (i.e., Ga and In), Group 11 metals (i.e., Cu, Ag, and Au), and Group 12 metals (i.e., Zn, Cd, and Hg). Noble metals (i.e., Pt, Pd, Ir, Rh, Os, Re, Ru, Mo, and W) may be desirable for use. Preferred functional metals include, for example, cadmium, cobalt, copper, gold, iron, mercury, molybdenum, nickel, osmium, palladium, platinum, rhenium, rhodium, ruthenium, silver, zinc, and mixtures thereof. Platinum is a highly preferred functional metal according to this invention.

Combinations or mixtures of catalytic forms of such noble or non-noble metals, such as combinations of Pt with Sn, may be used. The valence state of the metal is preferably reduced, e.g., when this component is in the form of an oxide or hydroxide. The reduced valence state of the functional metal may be attained, in situ, during the course of a reaction, when a reducing agent, such as hydrogen, is included in the feed to the reaction.

The functional metal may be incorporated into the catalyst by methods known in the art, such as ion exchange, impregnation, or physical admixture. For example, solutions of appropriate metal salts may be contacted with the remaining catalyst components, either before or after selectivation of the catalyst, under conditions sufficient to combine the respective components. The metal-containing salt is preferably water-soluble. Examples of such salts include chloroplatinic acid, tetraammine platinum complexes, platinum chloride, tin sulfate, and tin chloride. The metal may be incorporated in the form of a cationic, anionic, or neutral complex such as $Pt(NH_3)_4^{2+}$, and cationic complexes of this type will be found convenient for exchanging metals onto the zeolite. Anionic complexes such as the vanadate or metatungstate ions are also useful for impregnating metals into the zeolites. Incorporation is preferably undertaken in accordance with the method described in U.S. Pat. No. 4,312,790. After incorporation of the metal, the catalyst can then be filtered, washed with water, and calcined at temperatures of from 250° C. to 500° C.

The functional metal must be able to enter the pores of the catalyst, i.e., permeate into the catalyst, to be able to survive high temperature exposure, such as that associated with calcination or conversion conditions. Addition of the metal can be accomplished through mixing the catalyst with a solution, preferably aqueous, of an appropriate metal salt. The mixing can be performed at about ambient temperature or at elevated temperatures, e.g., through reflux. In certain circumstances several exchanges may be required to facilitate proper permeation of the desired metal. For example, in the case of an acidic form of a catalyst, e.g., HZSM-5, it may be desirable to perform first exchange to provide an ammonium form, i.e., $NH_4$-HZSM-5, with a second exchange to provide the metal form.

To illustrate, a platinum-modified catalyst can be prepared by first adding to the catalyst an aqueous solution of ammonium nitrate to convert the catalyst from the hydrogen form to the ammonium form. Subsequently, an aqueous solution of tetraamine platinum(II) nitrate or tetraamine platinum(II) chloride 3 to increase the catalyst activity.

Alternatively, a functionalized catalyst can be directly prepared by adding a hydrogen form of the catalyst to an aqueous solution of ammonium dichloroplatinate (or other comparable salt for other metals, e.g., ammonium hexachlororhodate). The mixture can then be refluxed, followed by washing, drying, and calcination as described.

The amount of functional metal may be that amount which increases the catalytic ability of the overall catalyst to catalytically hydrogenate or dehydrogenate an organic compound, e.g., ethylene, under sufficient hydrogenation or dehydrogenation conditions. This amount is referred to herein as a catalytic amount. The amount of the functional metal is suitably from about 0.001 wt % to 10 wt %, preferably from about 0.05 wt % to about 5 wt %, more preferably from about 0.1 wt % to about 2 wt %, based on the total weight of the modified catalyst. However the artisan will recognize that the required amount of the functional metal will vary with the nature of the component, with less of the highly active noble metals, particularly platinum, being required than of the less active base metals.

As noted above, the hydrogenation-dehydrogenation function provided by the functional metal can decrease the ethylbenzene by-product in hydrocarbon conversions. However, it has been observed with conventional functional metal-modified catalysts that ethylbenzene yield gradually increases as a function of time on stream (TOS). This is not completely understood, but is believed to be associated with a gradual migration of the functional metal out of the catalyst pores to the surface of the catalyst, where its functionality is lost. It has now been found that such gradual increase in ethylbenzene in the catalyst effluent can be substantially inhibited by using the method of the invention. It is belien ed that this observation may be associated with a substantial inhibition of the migration of the functional metal out of the catalyst that would otherwise occur with increasing time on stream.

Selectivation of Catalysts

Various methods are known in the art for increasing the selectivity of zeolite catalysts. One such method is to modify the catalyst by treatment with a "selectivating agent." For example, U.S. Pat. Nos. 5,173,461; 4,950,835; 4,927,979; 4,465,886; 4,477,583; 4,379,761; 4,145,315; 4,127,616; 4,100,215; 4,090,981; 4,060,568; and 3,698,157 disclose specific methods for contacting a catalyst with a selectivating agent containing silicon ("organosilicon compound"). U.S. Pat. Nos. 5,367,099; 5,382,737; 5,365,004; 5,403,800; and 5,406,015, and PCT Publication No. WO94/27934, also disclose methods for silicon-based selectivation of catalysts.

In accordance with one selectivation method, called "ex situ selectivation" or "preselectivation," catalyst is modified by being exposed to one or more treatments with a silicon compound in a liquid carrier, each treatment being followed by calcination of the treated material in an oxygen-containing atmosphere, e.g., air. Thus, the zeolite, e.g., HZSM-5, is treated at least once, preferably at least twice, with a fluid medium comprising a silicon compound and a carrier fluid. The carried fluid is then removed, e.g., evaporated, leaving a deposited residue of the silicon compound on the catalyst. Subsequently, the coated catalyst is calcined to convert the silicon-containing material to a silica material containing little or no residual carbon. These modified catalysts have been observed to have improved properties in hydrocarbon conversion processes.

In contrast, a distinct form of selectivation is performed with the catalyst in the reactor under reaction conditions. This type of selectivation is identified as in situ selectivation. In situ selectivation is also known as "trim selectivation," as it is typically (but not necessarily) performed ancillary to ex situ selectivation, to effect a secondary improvement of catalyst performance, i.e., to "trim" the catalyst after it has been preselectivated.

In situ selectivation protocols include passing a feed stream comprising hydrogen and an aromatic (e.g., toluene) or a paraffin (e.g., hexane or decane) and an organosilicon compound over the zeolite under "in situ selectivation conditions," i.e., conditions sufficient to deposit a residue of the organosilicon compound on the zeolite. Suitable organosilicon compounds include volatile organosilicon compounds having sufficient vapor pressure for proper deposition under in situ selectivation conditions. Toluene may comprise 50 wt % to 100 wt %, e.g., at least 80 wt %, of the hydrocarbons in the feedstock. Other hydrocarbons, such as benzene, xylenes and trimethylbenzenes, may also be present in the feedstock for in situ selectivation.

In situ selectivation protocols typically comprise conditions include temperatures ranging from about 100° C. to about 600° C., preferably from about 300° C. to about 500° C.; pressures ranging from about 0 to about 2000 psig, preferably from about 15 psig to about 800 psig; a $H_2$/HC mole ratio of from about 0 (i.e., no hydrogen is present) to about 20, preferably from about 1 to about 4; at a WHSV of from about 0.1 $hr^{-1}$ to about 1 00 $hr^{-1}$, preferably from about 0.1 $hr^{-1}$ to about 10 $hr^{-1}$. Upon thermolysis, a siliceous coating is deposited on the zeolite surface, eliminating surface activity and enhancing shape-selectivity.

The presence of a sufficient amount of hydrogen in the in situ-selectivation feedstock is necessary to prevent rapid aging of the catalyst during the selectivation process resulting in an excessive reduction in the catalyst activity, possibly accompanied by a reduction in selectivity for ethylbenzene conversion. This rapid aging is believed to result from a rapid build-up of excessive amounts of carbonaceous deposits (i.e., coke), which may even extend into the pore system of the zeolite in the catalyst. However, even when hydrogen is used in optimal fashion to prevent aging during the selectivation process, a small amount of carbonaceous deposit forms on the catalyst. As a result of this carbonaceous deposit, the elemental analysis of the in situ-selectivated catalyst reveals a carbon content significantly greater than the carbon content of the fresh catalyst prepared by the multiple impregnation method described herein. More particularly, the in situ-selectivated catalyst may contain at least 2 wt %, e.g., at least 4 wt %, of carbon by elemental analysis, whereas the catalyst prepared by the multiple impregnation method may contain less than 0.5 wt % of carbon as measured by elemental analysis. These weight percentages are expressed in terms of the weight of the entire catalyst including the zeolite, binder, and optional components, e.g., hydrogenation-dehydrogenation components.

As described herein, the present invention uses a new technique to selectivate the zeolite catalyst. The gradient selectivation protocol that Applicants have unexpectedly found to be useful according to the invention differs from conventional in situ selectivation in that conventional in situ selectivation is performed under conditions that accommodate efficient hydrocarbon conversion. Typically, an in situ selectivation temperature is established that substantially corresponds to a nominal conversion temperature, and an in situ selectivating agent is added to the hydrocarbon feed. At a later time, the in situ selectivating agent feed is stopped while the hydrocarbon conversion is continued. By contrast, the gradient selectivation protocol according to the invention requires a controlled modulation of conversion temperature marked by imposition of a temperature gradient during the period in which the selectivating agent is co-fed to the reactor.

Thus, the gradient selectivation protocol comprises an "increasing" temperature gradient or a "progressive" temperature gradient. By this is meant that a substantial portion of the in situ selectivation period is employed in exposing the catalyst to a temperature gradient wherein the conversion temperature is raised from a lower temperature to a higher temperature. The gradient may be continuous, semi-continuous, or stepped. If stepped, the gradient may have at least one intermediate temperature step, and preferably two or more temperature steps, at which the temperature is maintained for a period of time before being raised. Typically, stepped gradients are easier to control, and they are for this reason preferred. If a continuous gradient is employed, the gradient may be linear or nonlinear, e.g., "S" type curves or exponential curves. In certain cases wherein the conversion temperature is appropriate, the progressive temperature gradient may proceed from a temperature below a defined nominal conversion temperature to a temperature above the nominal conversion temperature.

Once the gradient is completed, the selectivating agent feed is terminated and the temperature is adjusted to the nominal conversion temperature whereupon the hydrocarbon conversion process is allowed to proceed. Other conversion parameters, e.g., space velocity, hydrogen content, pressure, etc., may be adjusted as needed following the gradient selectivation.

The lower and upper temperature bounds of the temperature gradient will depend upon the nature of the hydrocarbon conversion, as different conversion processes require different nominal conversion conditions for optimized yields. However, the temperature gradient will generally traverse a range of from about 15° C. to about 150° C., preferably from about 25° C. to about 100° C. The lower temperature bound may be from about 350° C. to about 460° C. preferably from about 380° C. to about 430° C. The upper temperature bound may be from about 420° C. to about 550° C., preferably from about 450° C. to about 510° C. Thus, for example, in a toluene disproportionation process, the nominal conversion temperature may be about 445° C., and the gradient selectivation method may comprise a lower temperature bound of about 410° C. and an upper temperature bound of about 490° C. For other hydrocarbon conversions, the skilled artisan will determine nominal conversion temperatures, and can adjust gradient upper and lower temperature bounds if desired.

The gradient selectivation procedure will generally have a duration of from about 20 hr to about 500 hr on stream, preferably from about 50 hr to about 200 hr on stream. For stepped gradients, comprising one or more intermediate temperature steps, the duration of each step may be selected independently of those of any other steps. Typically, each step will have a duration of from about 2 hr to about 100 hr, preferably from about 5 hr to about 75 hr. The temperature differential (the "rise") of each step may be selected by the artisan, typically ranging from about 1° C. to about 50° C., preferably from about 5° C. to about 20° C. The temperature differentials for each step may be the same or different.

Once the gradient selectivation is completed, the temperature is adjusted to about the nominal conversion temperature. However, the artisan can further adjust the conversion temperature (along with other conversion parameters) as desired to modify the conversion process, thereby modifying the product mix and yield. The artisan may further wish to maintain, adjust, or terminate the co-feed of the selectivating agent.

Despite the conventional understanding that in situ selectivation is useful as an adjunct to ex situ selectivation techniques, Applicants have unexpectedly found that a metal-functionalized catalyst can be effectively selectivated under reactor conditions including the progressive temperature gradient described herein, but without requiring any ex situ selectivation. As a result, the "gradient selectivation" referred to herein need not be associated with or preceded by a primary preselectivation procedure. Even so, it is possible, and may be desirable, to modify the catalyst of the invention by conducting an ex situ preselectivation procedure prior to the gradient selectivation described herein to further enhance conversion yields.

While not wishing to be bound by theory, it is believed that the advantages of the present invention are obtained by rendering acid sites on the external surfaces of the catalyst substantially inaccessible to reactants while increasing catalyst tortuosity. Acid sites existing on the external surface of the catalyst are believed to isomerize the p-xylene exiting the catalyst pores back to an equilibrium level with the other two isomers thereby reducing the amount of p-xylene in the xylenes to only about 24%. By reducing the availability of these acid sites to the p-xylene exiting the pores of the catalyst, the relatively high level of p-xylene can be maintained. It is believed that the high-efficiency, p-xylene selectivity agents of the present invention block or otherwise render these external acid sites unavailable to the p-xylene by chemically modifying the sites. Preferably, the kinetic diameter of the high efficiency, p-xylene selectivating agent is larger than the zeolite pore diameter, to avoid reducing the internal activity of the catalyst.

In line with this theory, it is also believed that the presence of hydrogen in the reaction zone is important to maintain the desired high yields of p-xylene when a silicone compound is used as the high-efficiency p-xylene selectivating agent. The importance of the hydrogen in the feedstock may be reduced in alternative embodiments by using a high efficiency p-xylene selectivating agent comprising a silane or some other compound which effectively renders the isomerizing acid sites on the external surface of the catalyst inaccessible.

Moreover, the progressive temperature gradient which is so beneficial in the present invention is believed to help maintain a high degree of metals dispersion by trapping the functional metal within the catalyst pores. Metal migration and agglomeration, which would otherwise result in loss of activity under hydrocarbon conversion conditions is thereby minimized. However, Applicants have unexpectedly observed that the progressive temperature protocol augments the beneficial functionality imparted to the catalyst through permeation with a functional metal as described is rendered substantially stable under conversion conditions. As a result, by-product yields are stabilized at extraordinarily low levels without increasing substantially with increasing time on stream. Thus, the catalysts modified according to the invention have substantially extended lifetimes. Furthermore, the catalysts of the invention are substantially stable to regeneration protocols, and may even not require regeneration to maintain their superior functionality.

The organosilicon compound used to selectivate the zeolite may be a silicone, siloxane, or silane. Silicones are defined herein as those compounds wherein silicon atoms are bonded to one another via oxygen atoms. Silanes are defined herein as those compounds wherein silicon atoms are bonded directly to one another. These organosilicon compounds may have at least 2 silicon atoms per molecule. The molecular weight of the silicon compound employed as a selectivating agent may be between 80 and 20,000, and is preferably within the approximate range of 150 to 10,000.

The kinetic diameter of the selectivating agent is preferably larger than the zeolite pore diameter, to avoid entry of the selectivating agent into the zeolite pores and any concomitant reduction in the internal activity of the zeolite.

When a silicon compound is used that is of a size small enough to enter the pores of the catalyst crystal, it may be desirable to use the sodium form of the zeolite rather than the hydrogen form.

The silicon compound used to gradient selectivate the present zeolite may be constructed of a siloxy backbone structure capped with terminal groups. This siloxy backbone structure may be a chain structure represented by the formula:

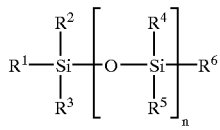

wherein $R^1$, $R^2$, $R^3$, $R^4$, $R^5$, and $R^6$ are independently selected from hydrogen, fluorine, hydroxy, alkyl, aralkyl, alkaryl, alkoxy, or fluoro-alkyl. The hydrocarbon substituents generally contain from 1 to 10 carbon atoms and preferably are methyl, ethyl, or phenyl groups. The variable n is an integer of at least 2, and generally in the range of from 2 to about 1000.

Preferred examples of silicone compounds having a chain siloxy backbone structure given above are those wherein $R^1$ and $R^6$ are independently hydrogen, methyl, or phenyl; $R^2$, $R^3$, $R^4$ and $R^5$ are independently methyl or phenyl; and m is from 1 to 100, e.g., from 1 to 25, e.g., from 1 to 10, e.g., from 1 to 4. Preferably, no more than one phenyl group is bonded to each silicon atom. Particular examples of such silicone compounds having a chain siloxy backbone structure include hexamethyldisiloxane, decamethyltetrasiloxane, and diphenyltetramethyldisiloxane.

Representative silicone compounds include dimethylsilicone, diethylsilicone, phenylmethylsilicone, methylhydrogensilicone, ethylhydrogensilicone, phenylhydrogensilicone, methylethylsilicone, phenylethylsilicone, diphenylsilicone, methyltrifluoropropylsilicone, ethyltrifluoropropylsilicone, polydimethylsilicone, tetrachlorophenylmethylsilicone, tetrachlorophenylethylsilicone, tetrachlorophenylhydrogensilicone, tetrachlorophenylphenylsilicone, methylvinylsilicone, and ethylvinylsilicone.

This siloxy backbone structure may also be a cyclic structure represented by the formula:

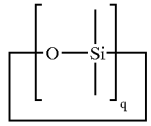

where q is from 2 to 10. Branched chain structures and composite chain/cyclic structures are also possible for the siloxy backbone of the silicone selectivating agent.

The silicone compound need not be linear, but may be cyclic, for example, hexamethylcyclotrisiloxane, octamethylcyclotetrasiloxane, hexaphenylcyclotrisiloxane, octaphenylcyclotetrasiloxane, and decamethylcyclopentasiloxane. Particular examples of silicone compounds having a branched siloxy backbone structure are tris-(trimethylsiloxy)-phenylsilane and tris-(trimethylsiloxy)-silane.

Usefull silanes, disilanes, or alkoxysilanes include organic-substituted silanes having the general formula:

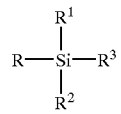

wherein R is a reactive group such as hydrogen, alkoxy, halogen, carboxy, amino, acetamide, or trialkylsilyl. $R^1$, $R^2$, and $R^3$ can be the same as R or an organic radical which may include $C_1$–$C_{40}$ alkyl; alkyl-or aryl carboxylic acid wherein the organic portion of the alkyl is a $C_1$–$C_{30}$ alkyl and the aryl group is a $C_6$–$C_{24}$ aryl; $C_6$–$C_{24}$ aryl groups which may be further substituted; alkylaryl; and $C_7$–$C_{30}$ arylalkyl groups. Preferably, the alkyl group of an alkyl silane is between 1 and 4 carbon atoms in chain length. Mixtures may also be used.

The silane compounds useful as selectivating agents according to the present method may have structures corresponding to the above-mentioned silicone compounds, except that the silicon atoms are bonded directly to one another instead of via oxygen atoms. Examples of silanes having a chain backbone structure include those of the formula:

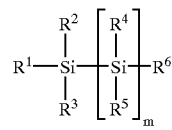

where $R^1$ and $R^6$ are independently hydrogen, methyl, or phenyl; $R^2$, $R^3$, $R^4$, and $R^5$ are independently methyl or phenyl; and m is from 1 to 100, preferably from 1 to 25, and more preferably from 1 to 4. The silanes or disilanes include, as non-limiting examples, dimethylphenylsilane, phenytrimethylsilane, triethylsilane, and hexamethyldisilane. Useful alkoxysilanes are those with at least one silicon-hydrogen bond.

Preferred organosilicon selectivating agents useful for selectivation of zeolites include dimethylphenylmethyl polysiloxane (e.g., Dow-550) and phenylmethyl polysiloxane (e.g., Dow-710). Dow-550 and Dow-710 are available from Dow Chemical Co., Midland, Mich.

As noted elsewhere herein, the catalyst can optionally be preselectivated by exposure to one or more ex situ selectivation treatments with a silicon compound in a liquid carrier, each treatment being followed by calcination of the treated material in an oxygen-containing atmosphere, e.g., air. Thus, the zeolite, e.g., HZSM-5, is treated at least once, preferably at least twice, more preferably at least 3 times, e.g., from 4 to 6 times, with a fluid medium comprising an silicon compound and a carrier fluid. The silicon compound may be present in the form of a solute dissolved in the liquid carrier or in the form of emulsified droplets in the liquid carrier. Generally, the organosilicon compounds suitable for use as selectivating agents in such preselectivation protocols are selected from the same compounds identified above as suitable for use in the requisite gradient selectivation.

The carrier fluid may be water, an organic fluid, or a combination thereof. Various organic compounds and combinations thereof have been employed as carrier fluids for the silicon selectivating agent. For example, U.S. Pat. Nos. 4,145,315; 4,127,616; 4,090,981; and 4,060,568 describe the use of inter alia $C_5$–$C_7$ alkanes as solvents for silicon impregnation. Such organic carriers may linear, branched, or cyclic hydrocarbons having five or more, especially 7 or more, carbon atoms per molecule, e.g., alkanes, such as heptane, octane, nonane, decane, undecane, and dodecane. Mixtures of low volatility organic compounds, such as hydrocracker recycle oil, may be employed as carriers. Particularly preferred organic carriers are decane and dodecane.

When water is used as the carrier medium, the organosilicon compound may be distributed therein in solution or in emulsion form. Particularly when the liquid medium comprises an emulsion of the silicon compound in water, the carrier medium may also comprise an emulsifying agent, such as a surfactant. When the organosilicon preselectivating agent is present in the form of a water soluble compound in an aqueous solution, the organosilicon compound may be substituted with or more hydrophilic functional groups or moieties, which serve to promote the overall water solubility of the organosilicon compound. These hydrophilic functional groups may include one or more organoarine groups, such as $—N(CH_3)_3$, $—N(C_2H_5)_3$, and $—N(C_3H_7)_3$. A preferred water-soluble organosilicon preselectivating agent is an n-propylamine silane, available as Hydrosil 2627 from Huils America. Particular water-soluble organosilicon compounds, which may be used for multiple impregnations of the present catalyst, are referred to as aminosilane polymers in U.S. Pat. No. 5,371,312.

When the zeolite is preselectivated by a single or multiple impregnation technique, the zeolite is calcined after each impregnation to remove the carrier and to convert the liquid organosilicon compound to a solid residue material thereof This solid residue material is referred to herein as a siliceous solid material, insofar as this material is believed to be a polymeric species having a high content of silicon atoms in its structure. However, this siliceous solid residue material may also comprise residual carbon atoms in its structure, resulting from the organic portion of the organosilicon compound.

Following each impregnation, the zeolite may be calcined, by heating at a rate of from 0.2° C./min to 5° C./min, to a temperature greater than 200° C., but below the temperature at which the crystallinity of the zeolite is adversely affected. This calcination temperature is typically below about 600° C., generally being within the approximate range of 350° C. to 550° C. The duration of calcination at the calcination temperature may be from 1 hr to 24 hr, e.g., from 2 hr to 6 hr.

The impregnated zeolite may be calcined in an inert or oxidizing atmosphere. An example of such an inert atmosphere is a nitrogen ($N_2$) atmosphere. An example of an oxidizing atmosphere is an oxygen containing atmosphere, such as air. Calcination may take place initially in an inert, e.g., $N_2$ atmosphere, followed by calcination in an oxygen containing atmosphere, such as air or a mixture of air and $N_2$. Calcination should be performed in an atmosphere substantially free of water vapor to avoid undesirable uncontrolled steaming of the zeolite. The zeolite may be calcined once or more than once following each impregnation. The various calcinations following each impregnation need not be identical, but may vary with respect to the calcination temperature, the rate of temperature rise, the atmosphere, and the duration of calcination.

The amount of siliceous residue material that is deposited on the zeolite or bound zeolite is dependent upon a number of factors including the temperatures of the impregnation and calcination steps, the concentration of the organosilicon compound in the carrying medium, the degree to which the catalyst has been dried prior to contact with the organosilicon compound, the atmosphere used in the calcination, and duration of the calcination. A suitable amount of silicon on the catalyst is greater than 9 wt %, e.g., greater than 12 wt %, exclusive of the silica present in the binder or in the zeolite itself.

The catalyst may be subjected to steaming conditions sufficient to increase or decrease the activity and/or selectivity of the catalyst as desired. Such conditions are disclosed, for example, in U.S. Pat. No. 5,349,114. The steaming conditions may include a temperature of from about 100° C. to about 800° C., e.g., from about 175° C. to about 325° C., with from about 1% to about 100% steam, e.g., from about 50% to about 100% steam, at a pressure of from about 0.01 psia (69 Paa) to about 5000 psia (34474 kPaa), and for a duration of from about 0.1 hr to about 24 hr, e.g., from about 3 hr to about 6 hr. Excessive steaming or steaming under severe conditions may be detrimental to the activity and selectivity of the catalyst.

The present catalyst may be further modified to comprise at least 0.03 wt %, e.g., at least 0.1 wt %, of alkali metal or alkaline earth metal, e.g., an amount effective to achieve the desired activity/selectivity. Particular alkali metals include Li, Na, K, Rb, and Cs. Particular alkaline earth metals include Mg, Ca, Sr, and Ba. The alkali metal or alkaline earth metal may be added by contacting the catalyst, in particular, the zeolite component of the catalyst, either before or after selectivation, with an aqueous solution containing an alkali metal, ion of an alkali metal, alkaline earth metal, or ion of an alkaline earth metal, optionally washing off excess solution using water or another solvent, and then drying the treated catalyst. The present alkali metal or alkaline earth metal incorporation or ion exchange procedure may be used to decrease the activity of the catalyst. The activity may be adjusted on a small scale to fine-tune batches of the catalyst for a particular use or the activity may be adjusted on a major scale to convert the catalyst from one type to another, thereby providing a means to manufacture different catalysts for different uses. The amount of alkali metal or alkaline earth metal ions incorporated into the catalyst will generally negatively affect catalyst activity, and can be selected as desired to fine-tune the activity of the catalyst. Thus, smaller amounts of alkali metal or alkaline earth metal will reduce the alpha value of the catalyst by a smaller amount, e.g., about 10%, and larger amounts of alkali metal or alkaline earth metal will reduce the alpha value of the catalyst by a larger amount, e.g., by 50% or more.

The present catalyst may be subjected to controlled coking. This controlled coking procedure is also referred to herein as coke selectivation. This optional coke selectivation may involve contacting the catalyst with a thermally decomposable organic compound at an elevated temperature in excess of the decomposition temperature of the compound but below the temperature at which the crystallinity of the zeolite is adversely affected. This contact temperature may be, for example, less than 650° C. The catalyst may be coked in a reactor or other vessel that is different than that used for the ethylbenzene conversion, followed by transport of the coked catalyst to the ethylbenzene conversion reactor. Performance of coke selectivated catalyst for ethylbenzene conversion is not significantly degraded by the handling associated with transporting the catalyst between the reactor used to coke sejectivated the catalyst and the ethylbenzene conversion catalyst. Coke selectivation is described in U.S. Pat. Nos. 5,234,875; 4,581,215; 4,508,836; 4,358,395; 4,117,026; and 4,097,543.

Organic materials useful for this coke selectivation process encompass a wide variety of compounds, including by way of example, hydrocarbons, such as paraffins, cycloparaffins, olefins, cycloolefins and aromatics; oxygen-containing organic compounds, such as alcohols, aldehydes, ethers, ketones and phenols; and heterocyclics, such as furans, thiophenes, pyrroles and pyridines. A hydrogen co-feed may be used to deter the excessive build-up of coke. Further details regarding coke selectivation techniques are provided in the U.S. Pat. No. 4,117,026, as well as in PCT Publication No. WO94/27934. An organosilicon cofeed may be, optionally, included along with the organic material feed used for coke selectivation. this organosilicon material may be selected from the organosilicon compounds mentioned hereinabove for use in the in situ selectivation of the catalyst.

Shape-Selective Hydrocarbon Conversion Processes

The functionalized catalyst according to the invention has exemplary utility in toluene disproportionation processes, to yield high purity-xylene with ethylbenzene by-product yields that are substantially reduced over those possible using conventional processes. The functionalized catalyst can also be used in other hydrocarbon conversion processes including, for example, lube dewaxing (e.g., MLDW), isomerization dewaxing (e.g., MIDW), paraffin dehydrogenation, ethylbenzene conversion, M2-forming, reforming, paraffin isomerization, NOx reduction, and methanol reduction to aromatics.

Toluene disproportionation is representative of shape-selective conversions. Although the present invention is described herein in terms of disproportionation, the present invention also applies to other related conversions such as methylation reactions, e.g., those using methylhalides and methylethers. Normally a single pass conversion of a toluene stream results in a product stream which includes dimethylbenzenes having alkyl groups at all locations, i.e., ortho-, meta-, and para-xylenes. Furthermore, the xylenes are known to proceed in a reaction which produces unwanted ethylbenzenes (EB). Without shape-selective control of this conversion process, the yield of p-xylene in a single pass has been limited by thermodynamics to approximately 8.2% when isomerization is permitted. This efficiency is reduced somewhat by the production of ethylbenzene.

The present invention provides high efficiency toluene conversion which reduces production of ortho- and meta-xylene isomers to the benefit of the desired para-xylene isomer. The resulting product stream preferably contains α-xylene purity of at least 94%, more preferably at least 95%, and most preferably at least 97%. For example, the o-xylene isomer can be reduced to not more than about 0.5% of the total xylene content while the m-xylene isomer can be reduced to less than about 5% of the total xylene content. Moreover, the presence of ethylbenzene can be significantly reduced, e.g., to less than about 2% of the $C_8$ product.

The toluene feedstock preferably comprises about 50% to 100% toluene, more preferably at least about 80% toluene. Other compounds such as benzene, xylenes, and trimethylbenzenes may also be present in the toluene feedstock without adversely affecting the present invention.

According to the process of this invention, the toluene feedstock may also be dried, if desired, in a manner which will minimize moisture entering the reaction zone. Methods known in the art suitable for drying the toluene charge for the present process are numerous. These methods include percolation through any suitable desiccant, for example, silica gel, activated alumina, molecular sieves or other suitable substances, or the use of liquid charge dryers.

Operating conditions employed in the improved process of the present invention will affect the reaction rate, para-selectivity, and conversion. Such conditions include the temperature; pressure, space velocity, and the $H_2$/HC mole ratio. Conditions effective for accomplishing the high para-selectivity and acceptable toluene disproportionation conversion rates include a reactor inlet temperature of from about 350° C. to about 540° C., preferably greater than about 400° C., a pressure of from about atmospheric (0 psig) to about 5000 psig, preferably from about 100 to about 1000 psig, a WHSV of from about 0.1 to about 20, preferably from about 2 to about 4, and a $H_2$/HC mole ratio of from about 0.1 to about 20, preferably from about 2 to about 4. This process may be conducted in either fixed or fluid-bed mode with attendant benefits of either operation readily obtainable.

The effluent is separated and distilled to remove the desired product, i.e., p-xylene, plus other by-products. The unreacted reactant, i.e., toluene, is preferably recycled for further reaction. The benzene is a valuable co-product.

The subject catalysts have good cracking and hydrocracking activity and may also be used to convert paraffins from high to low molecular weight substances in dewaxing processes. The catalysts of the invention may be used in processes such as those described, for example, in U.S. Pat. Nos. 3,700,585, Re. 28,398, 3,968,024 and 4,181,598, which are incorporated herein by reference.

The modified catalysts of the invention are also advantageously used in the isomerization of alkylaromatics, e.g., xylene isomerizations, ethylbenzene conversions, etc, such as conversion reactions described, for example, in U.S. Pat. Nos. 3,856,872, 3,856,873, Re. 30,157, 4,101,595, 4,101,597, 4,312,790, Re. 31,919, and 4,224,141, which are each herein incorporated by reference.

The catalyst can further be used for the conversion of aliphatic oxygenates to higher molecular weight compounds in a method as described in U.S. Pat. No. 4,476,330, incorporated by reference herein.

The modified catalysts of the invention are advantageously used in the oligomerization of olefins to form gasoline, distillate, lube oils, or chemicals in conversion reactions of the type described, for example, in U.S. Pat. Nos. 4,517,399, 4,520,221, 4,547,609, and 4,547,613, which are each herein incorporated by reference.

The modified zeolite catalysts of the invention are advantageously used in the conversion of aromatic compounds to provide dialkyl-substituted benzene products which are highly enriched in the para-dialkyl-substituted benzene isomer. Conversion reactions of this type include aromatics alkylation, transalkylation and disproportionation. Aromatics alkylations in which the catalysts of the invention can be used are described, for example, in U.S. Pat. Nos. 3,755,483, 4,086,287, 4,117,024, and 4,117,026, all of which are herein incorporated by reference.

The modified catalysts of the invention may also be used in the conversion of light paraffins and olefins to aromatics in processes of the type described, for example, in U.S. Pat. Nos. 3,760,024 and 3,756,942, which each are herein incorporated by reference.

The modified catalysts of the invention are also advantageously used in the synthesis of pyridine. Pyridine bases may be produced through the reactions of aldehydes and ketones with ammonia. Pyridine synthesis is described, for example, in U.S. Pat. No. 4,675,410 and U.S. Pat. No. 4,220,783, which are each herein incorporated by reference.

Caprolactam is used in the commercial production of nylon. Caprolactam may be produced by Beckmann rearrangement of cyclohexane oxime over acid catalysts including zeolites. The synthesis of caprolactam is described, for example, in U.S. Pat. No. 4,359,421, which is herein incorporated by reference.

Therefore, the modified catalysts of the present invention are suitable for use in a variety of shape-selective hydrocarbon conversion processes including as non-limiting examples:

Cracking hydrocarbons with reaction conditions including a temperature of from about 300° C. to about 700° C., a pressure of from about 0.1 atm (bar) to about 30 atm, and a WHSV of from about 0.1 hr$^{-1}$ to about 20 hr$^{-1}$;

Dehydrogenating hydrocarbon compounds with reaction conditions including a temperature of from about 300° C. to about 700° C., a pressure of from about 0.1 atm to about 10 atm, and WHSV of from about 0.1 hr$^{-1}$ to about 20 hr$^{-1}$;

Converting paraffins to aromatics with reaction conditions including a temperature of from about 300° C. to about 700° C., a pressure of from about 0.1 atm to about 60 atm, a WHSV of from about 0.5 hr$^{-1}$ to about 400 hr$^{-1}$, and a H$_2$/HC mole ratio of from about 0 to about 20;

Converting olefins to aromatics, e.g., benzene, toluene and xylene, with reaction conditions including a temperature of from about 100° C. to about 700° C., a pressure of from about 0.1 atm to about 60 atm, a WHSV of from about 0.5 hr$^{-1}$ to about 400 hr$^{-1}$, and a H$_2$/HC mole ratio of from about 0 to about 20;

Converting alcohols, e.g., methanol, or ethers, e.g., dimethylether, or mixtures thereof to hydrocarbons including olefins and/or aromatics with reaction conditions including a temperature of from about 275° C. to about 600° C., a pressure of from about 0.5 atm to about 50 atm, and aLHSV of from about 0.5 hr$^{-1}$ to about 100 hr$^{-1}$;

Isomerizing xylene feedstock components with reaction conditions including a temperature of from about 230° C. to about 51 0° C., a pressure of from about 3 atm to about 35 atm, a WHSV of from about 0.1 hr$^{-1}$ to about 200 hr$^{-1}$, and a H$_2$/HC mole ratio of from about 0 to about 100;

Disproportionating toluene with reaction conditions including a temperature of from about 200° C. to about 760° C., a pressure from about 1 atm to about 60 atm, and a WHSV of from about 0.08 hr$^{-1}$ to about 20 hr$^{-1}$;

Alkylating aromatic hydrocarbons, e.g., benzene and alkylbenzenes in the presence of an alkylating agent, e.g., olefins, formaldehyde, alkyl halides and alcohols, with reaction conditions including a temperature of from about 250° C. to about 500° C., a pressure of from about 1 atm to about 200 atm, a WHSV of from about 2 hr$^{-1}$ to about 2000 hr$^{-1}$, and an aromatic hydrocarbon/alkylating agent mole ratio of from about 1/1 to about 20/1; and Transalkylating aromatic hydrocarbons in the presence of polyalkylaromatic hydrocarbons with reaction conditions including a temperature of from about 340° C. to about 500° C., a pressure of from about 1 atm to about 200 atm, a WHSV of from about 10 hr$^{-1}$ to about 1000 hr$^{-1}$, and an aromatic hydrocarbon/polyalkylaromatic hydrocarbon mole ratio of is from about 1/1 to about 16/1.

In general, therefore, catalytic conversion conditions over a catalyst comprising the modified zeolite include a temperature of from about 100° C. to about 760° C., a pressure of from above 0 psig to about 3000 psig, a WHSV of from about 0.08 hr$^{-1}$ to about 2000 hr$^{-1}$ and a hydrogen/organic (e.g., hydrocarbon compound) mole ratio of from 0 to about 100.

The following examples are provided to assist in a further understanding of the invention. The particular materials and conditions employed are intended to be further illustrative of the invention and are not limiting upon the reasonable scope thereof.

EXAMPLE 1

A HZSM-5 catalyst was functionalized by adding platinum as a hydrogenation-dehydrogenation metal. A catalyst preparation was designed to yield a functionalized catalyst containing 0.05 wt % platinum. Thirty grams (30 g) of HZSM-5 was added to 150 mL of a 1 M aqueous solution of NH$_4$NO$_3$. The pH of the mixture was adjusted to pH 8–9 with dilute NH$_4$OH. The mixture was then placed on an orbital stirrer and stirred for 1 hr. Then a solution of 0.0300 g tetraamine platinum(II) nitrate in 1.0 mL water as added to the mixture. The mixture was placed on an orbital stirrer and stirred overnight. The catalyst mixture was then filtered, rinsed with distilled water, and dried at 150° C. for 1 hr. Finally, the functionalized catalyst (Pt-HZSM-5) was program calcined in air at 5° C./min to 350° C., then held for 3 hr at 350° C.

EXAMPLE 2

Two grams (2.0 g) of Pt-HZSM-5 catalyst prepared as described in Example 1 was in situ selectivated according to a conventional protocol, using a 2% solution of hexamethyldisiloxane in toluene. The selectivation conditions included a temperature of 447° C., a pressure of 500 psig, a WHSV of 4 hr$^{-1}$, and H$_2$/HC ratio of 2. During 54 hr selectivation time, p-xylene selectivity increased from 24% of the xylenes (thermodynamic equilibrium proportion) to 96.4% at 30% conversion. However, over the same time on stream, ethylbenzene make increased gradually from 0.5 wt % to 5.2 wt % based on the total C$_8$ product.

EXAMPLE 3

A 2.0 g sample of Pt-HZSM-5 catalyst prepared as described in Example 1 was gradient selectivated according to the method of the invention. In this case the gradient selectivation was performed generally in accordance with the conditions described in Example 2, except that a progressive temperature gradient was employed over the course of the selectivation period. The following stepped gradient program was used:

TABLE 1

| Selectivation Temperature (° C.) | Hours at Selectivation Temperature |
| --- | --- |
| 415 | 48 |
| 430 | 45 |
| 445 | 53 |
| 465 | 22 |
| 485 | 6 |

When the gradient selectivation was complete, the temperature was lowered to 430° C. and the WHSV was lowered to 3 hr$^{-1}$, while retaining H$_2$/HC=2.

During the gradient selectivation, the p-xylene selectivity increased from the thermodynamic 24 wt % of the xylenes to 98.6 wt %, at 23% conversion. In contrast to the catalyst described in Example 2, ethylbenzene selectivity did not increase with time on stream, but actually decreased somewhat, from 0.6% to 0.4% of the C$_8$ product. The ethylbenzene make remained constant for 6 days on stream. Following an air regeneration procedure (1° C./min to 538° C., then hold at 538° C. for 1.5 hr), conversion was resumed, using the same conversion conditions, with ethylbenzene selectivity at 0.4%. This result indicates that the functionalized catalyst according to the invention was substantially stable under conversion conditions.

EXAMPLE 4

The catalyst of the invention also improves ethylbenzene conversion processes. In this example, an unselectivated platinum-modified catalyst representative of the prior art was compared to a gradient selectivated platinum-modified catalyst of the invention, The ethylbenzene conversion was performed using a feed consisting of 20 wt % ethylbenzene, 60 wt % m-xylene, and 20 wt % o-xylene. The results of this experiment are illustrated in Table 2, below. Conventional conversion conditions were used: 427° C., 150 psig, and $H_2/HC=1$, with WHSV as indicated in the Table.

TABLE 2

| Yield (wt %) | Prior Art WHSV = 20 | Gradient Selectivated WHSV = 10 | Gradient Selectivated WHSV = 20 |
|---|---|---|---|
| $C_5^-$ | 3.6 | 4.7 | 3.4 |
| Benzene | 9.8 | 11.9 | 8.8 |
| Toluene | 2.9 | 0.8 | 0.3 |
| Ethylbenzene | 5.4 | 2.8 | 6.4 |
| p-Xylene | 17.0 | 0.1 | 0.1 |
| m-Xylene | 42.5 | 59.6 | 60.3 |
| o-Xylene | 18.0 | 20.0 | 20.6 |
| $C_9^+$ | 1.0 | 0.0 | 0.0 |
| Ethylbenzene Conversion (%) | 73 | 86 | 68 |
| Xylene Conversion (%) | 3.3 | 0.3 | <0.1 |
| Toluene + $C_9^+$ (wt %) | 3.9 | 0.8 | 0.3 |

Compared to the test results for the non-selectivated prior art catalyst, the functionalized catalyst of the invention significantly reduced xylene loss from 3.3% to essentially zero. Also, the functionalized catalyst was effective to reduce by-products (toluene+$C_9^+$) by an order of magnitude, i.e., from 3.9 wt % to 0.3 wt %. These results were obtained at similar ethylbenzene conversion levels (68% vs. 73%).

Moreover, by lowering the WHSV from 20 $hr^{-1}$ to 10 $hr^{-1}$, the ethylbenzene conversion over the catalyst of the invention increased significantly to 86%. The xylene loss and by-product make each increased only slightly to 0.3% and 0.8 wt %, respectively, but these amounts are still substantially less than those produced by the conventional catalyst.

Thus, while there have been described what are presently believed to be the preferred embodiments of the present invention, those skilled in the art will realize that other and further embodiments can be made without departing from the spirit of the invention, and it is intended to include all such further modifications and changes as come within the true scope of the claims set forth herein.

What is claimed is:

1. A catalyst for use in shape-selective hydrocarbon conversion processes, wherein the catalyst has been modified according to the procedure comprising the steps of:
    (a) permeating a catalytic amount of a hydrogenation-dehydrogenation functional metal into a catalytic molecular sieve to provide a metal-modified catalyst, and
    (b) selectivating the metal-modified catalyst under an in situ selectivation protocol to provide a functionalized catalyst, wherein, to enhance the stability of said functional metal during subsequent use in a hydrocarbon conversion process, said in situ selectivation protocol includes the steps of contacting said metal-modified catalyst with a silicon selectivating agent at a plurality of different and increasing temperatures and maintaining said metal-modified catalyst in contact with the silicon selectivating agent at each of said different temperatures for a time of at least about 2 hours.

2. The catalyst according to claim 1, wherein the permeating step comprises permeating into said catalytic molecular sieve a functional metal which is one or more metals from Groups 3 to 15 of the Periodic Table.

3. The catalyst according to claim 1, wherein the permeating step comprises permeating into said catalytic molecular sieve a functional metal which is platinum, palladium, nickel, copper, cobalt, molybdenum, rhodium, ruthenium, silver, gold, mercury, osmium, iron, zinc, cadmium, or mixtures thereof.

4. The catalyst according to claim 1, wherein the catalytic molecular sieve comprises a zeolite which is ZSM-5, ZSM-11, ZSM-12, ZSM-21, ZSM-22, ZSM-23, ZSM-35, ZSM-38, ZSM-48, ZSM-57, or ZSM-58.

5. The catalyst according to claim 1, wherein the metal-modified catalyst is maintained in contact with the silicon selectivating agent at each of said different temperatures for a time of from about 2 hours to about 100 hours.

6. The catalyst according to claim 1, wherein the in situ selectivation protocol includes the steps of contacting the metal-modified catalyst with a silicon selectivating agent at a lower temperature in the range of from about 350° C. to about 460° C., and an upper temperature in the range of from about 420° C. to about 550° C.

7. The catalyst according to claim 6, wherein the lower temperature range is from about 380° C. to about 430° C., and the upper temperature range is from about 450° C. to about 510° C.

8. The catalyst according to claim 1, wherein the in situ selectivation protocol further comprises a pressure of from above 0 psig to about 2000 psig, a $H_2/HC$ mole ratio of from 0 to about 100, and a WHSV of from about 0.08 $hr^{-1}$ hr to about 2000 $hr^{-1}$.

9. The catalyst according to claim 1, wherein the procedure further comprises preselectivating the catalyst by exposing the catalyst to at least one preselectivation sequence, each preselectivation sequence comprising contacting the catalyst with an organosilicon compound and then calcining the contacted catalyst.

10. A process for shape-selective hydrocarbon conversion, comprising converting a hydrocarbon under conversion conditions over a functionalized catalyst of claim 1, wherein product yield and distribution from the hydrocarbon conversion over the functionalized catalyst is substantially stable with increasing time on stream.

11. A process according to claim 10, wherein the conversion conditions for the hydrocarbon conversion comprise a temperature of from about 100° C. to about 760° C., a pressure of from above 0 psig to about 3000 psig, a $H_2/HC$ mole ratio of from 0 to about 100, and a WHSV of from about 0.08 $hr^{-1}$ to about 2000 $hr^{-1}$.

* * * * *